(12) United States Patent
Shimizu et al.

(10) Patent No.: US 6,620,935 B1
(45) Date of Patent: Sep. 16, 2003

(54) PROCESS FOR PRODUCING BENZYLAMINE COMPOUND

(75) Inventors: Takanori Shimizu, Funabashi (JP); Shiro Kawahara, Funabashi (JP); Takashi Horiuchi, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 10/111,421

(22) PCT Filed: Nov. 10, 2000

(86) PCT No.: PCT/JP00/07962

§ 371 (c)(1), (2), (4) Date: May 7, 2002

(87) PCT Pub. No.: WO01/34588

PCT Pub. Date: May 17, 2001

(30) Foreign Application Priority Data

Nov. 11, 1999 (JP) ............................................. 11-321023

(51) Int. Cl.[7] ...................... C07D 241/04; C07D 295/04
(52) U.S. Cl. ....................................................... 544/391
(58) Field of Search ......................................... 544/391

(56) References Cited

U.S. PATENT DOCUMENTS

| | | | |
|---|---|---|---|
| 4,291,060 A | | 9/1981 | Kraska ........................ 424/316 |
| 5,728,702 A | * | 3/1998 | Tanikawa et al. ........... 514/253 |

FOREIGN PATENT DOCUMENTS

| | | |
|---|---|---|
| JP | 06-072968 | 3/1994 |
| WO | 95/01343 | 1/1995 |

OTHER PUBLICATIONS

George P. Rizzi: "A novel syntheis of benzylamines from benzaldehydes" J. Org. Chem., vol. 36, No. 12, pp. 1710–1711 1971.

Chemical Abstracts, E. Takagi, et al., vol. 46, No. 17, 1 page, XP–002216290, "Reaction Between Aromatic Aldehydes and Alpha–Amino Acids (II). A New Reaction Giving Alkamines and 1,2–Diphenylethanolamine Series (1)", Sep. 10, 1952.

Chemical Abstracts, E. Takagi, et al., vol. 48, No. 17, 1 page, XP–00221629, "Reactions Between Aromatic Aldehydes and Alpha–Amino Acids", Sep. 10, 1954.

* cited by examiner

Primary Examiner—Mukund J. Shah
Assistant Examiner—Zachary C. Tucker
(74) Attorney, Agent, or Firm—Oblon, Spivak, McClelland, Maier & Neustadt, P.C.

(57) ABSTRACT

A process for producing a benzylamine compound represented by formula (2), which comprises reacting a benzaldehyde compound represented by formula (1) with an amino acid in the presence of an acid.

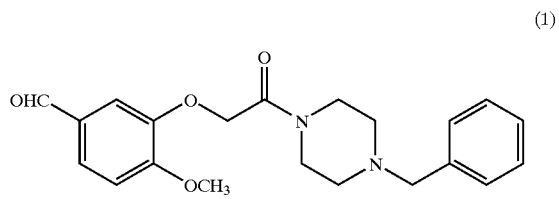

(1)

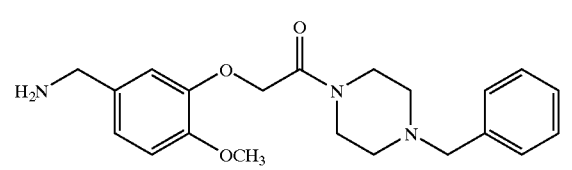

(2)

5 Claims, No Drawings

PROCESS FOR PRODUCING BENZYLAMINE COMPOUND

This Application is the U.S. National Stage, filed under 35 U.S.C. 371, of PCT/JP00/07692, filed Nov. 10, 2000.

TECHNICAL FIELD

The present invention relates to a novel process for producing a benzylamine compound important as an intermediate for the following pyridazinone compound (3) useful as a medicine.

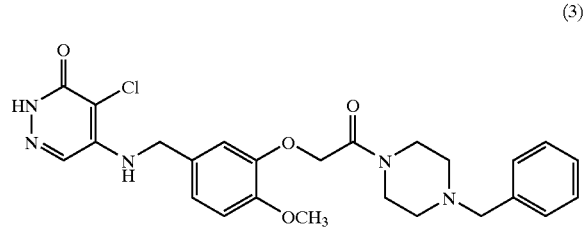

(3)

BACKGROUND ART

WO95/01343 and Japanese Unexamined Patent Publication JP-A-8-041033 disclose the pyridazinone compound (3) as a useful medicine having a bronchodilator action, an anti-allergic action and an antiplatelet action.

The compound (2), the important intermediate for synthesis of the pyridazinone compound (3), has been produced from isovanilline (4) in accordance with the following reaction scheme.

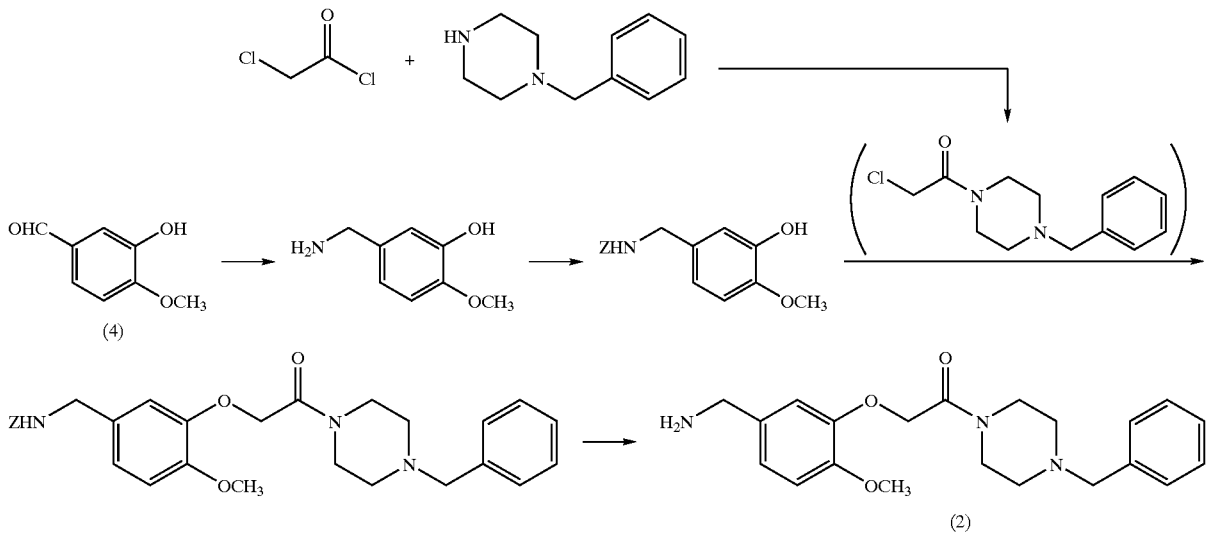

The above-mentioned process comprises several steps and entails cumbersome operations.

Especially, the use of benzyloxycarbonyl (Z) as the protecting group requires not only additional two steps for its introduction and removal but also expensive reagents such as benzyloxycarbonyl chloride (ZCl). Therefore, it is demanded to establish a process which uses no protecting group from the operational and economical standpoints.

DISCLOSURE OF THE INVENTION

The present inventors proposed a direct conversion route from the compound (1) to the benzylamine compound (2) as a solution to the above-mentioned problems and, as a result of their extensive research, have found out that the compound (2) can be obtained in a high yield by using various amino acids in the reaction.

Namely, the present invention provides a process for producing a benzylamine compound represented by formula (2), which comprises reacting a benzaldehyde compound represented by formula (1) with an amino acid in the presence of an acid.

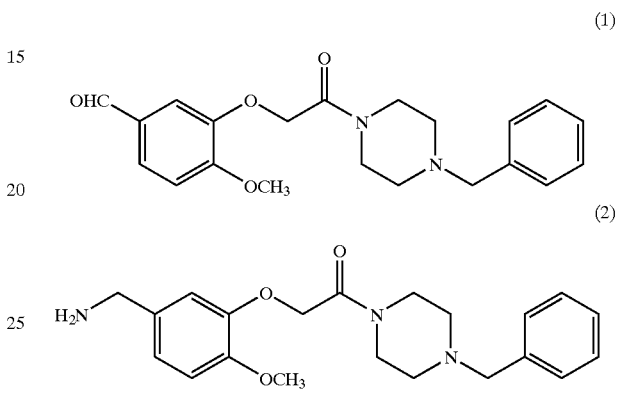

The novel process of the present invention is operationally advantageous because it can skip two steps in the conventional process. Besides, it is economically advantageous because it does not require an expensive protecting reagent.

BEST MODE FOR CARRYING OUT THE INVENTION

According to the present invention, the benzaldehyde compound (1) converts into the benzylamine compound (2) when heated with various amino acids.

Preferable examples of the process of the present invention are recited below.

(1)

A process for producing the benzylamine compound represented by formula (2), which comprises reacting the benzaldehyde compound represented by formula (1) with an amino acid in the presence of hydrochloric acid.

(2)

The process according to (1) wherein the amino acid is valine or 2-aminoisobutyric acid.

(3)

The process for producing a benzylamine compound according to (1), wherein the reaction solvent is N,N-dimethylacetamide.

(4)

The process for producing a benzylamine compound according to (1) or (3), wherein the amount of hydrochloric acid is from two to three equivalents of the amount of the benzaldehyde compound.

Now, the process will be described concretely.

The desired benzylamine compound represented by formula (2) is obtainable by heating the benzaldehyde compound represented by formula (1), an amino acid and an acid in a solvent.

If the heating is so conducted that the low-boiling components formed in the reaction system evaporate, the same result (yield) can be obtained with a smaller amount of an amino acid than when the low-boiling components are not evaporated.

The solvent may be, though there is no particular restriction, an alcoholic solvent such as methanol or ethanol, a polar solvent such as N,N-dimethylacetamide or N,N-dimethylformamide or an aromatic organic solvent such as toluene or dichlorobenzene. N,N-dimethylacetamide is the best, but any other solvent may be used without particular restrictions.

Though there is no particular restrictions on the amount of a solvent, too much of a solvent tends to result in a lower yield, while in an excessively small amount of a solvent, the operations in mass production tend to be more difficult because stirring is tougher, and the product tends to be recovered as crystals with poor purity. Therefore, a solvent is used in an amount of from 3 to 10 times the weight of the compound (1).

Though any acid that has a high acidity and does not cause side reactions may be used without particular restrictions, as the acid, an inorganic acid such as hydrochloric acid or sulfuric acid or an organic acid such as methanesulfonic acid, trifluoromethanesulfonic acid or p-toluenesulfonic acid, preferably hydrochloric acid, may be mentioned.

With respect to the amount of an acid, at least 1 equivalent of an acid, based on the benzylamine compound (1), is required, but there is no particular upper limit on the amount of the acid. However, the amount of an acid is preferably from 2 to 3 equivalents based on the benzylamine compound (1), because too much of an acid produces economical and operational problems and the possibility of hydrolysis of the compound.

Because the above-mentioned amount means the amount of an acid present in the reaction system, when a salt of the benzylamine compound (1) is used as a substrate, for example, the preferable amount of an external acid to be added is from 1 to 2 equivalents.

As to specific examples of an acid to be added, for hydrochloric acid, 1 mol/L hydrochloric acid-dioxane solution, 10% (w/w) hydrochloric acid-ethanol solution and 35% concentrated hydrochloric acid may be mentioned as preferable examples, though there is no particular restriction.

Any common amino acid may be used without any particular restriction.

Specific examples include glycine, alanine, valine, leucine, isoleucine, serine, threonine, cysteine, phenylalanine and 2-aminoisobutyric acid. Valine and 2-aminoisobutyric acid are preferred in view of yield and operations.

Though there is no particular restriction on the amount of an amino acid, if the amount is less than 2 moles based on the compound (1), the yield is likely to be low. However, heating the reaction system with evaporation of the low-boiling components formed in the reaction system makes it possible to reduce the amount of an amino acid to 1.5 moles without loss in yield. The upper limit is preferably from 1.5 moles to 3 moles from the economical and operational standpoints, though there is no particular restriction.

As to the steric configuration of the amino acid, a d-, l- or dl-amino acid may be used with no problem.

Though the reaction may be conducted in any temperature range that allows the progress of the reaction and does not cause decomposition without any particular restriction, the reaction temperature range is from 100° C. to 250° C., preferably from 110° C. to 200° C.

Though the reaction time greatly depends on the reaction temperature, a reaction time of from 0.5 to 10 hours, preferably from 1 to 5 hours or longer is enough at a reaction temperature of 150° C.

The benzylamine compound (2) is obtained as a salt with the acid present in the reaction system.

When the salt is crystalline, the salt of the benzylamine compound (2) can be recovered with high purity directly by filtration followed by washing with a solvent such as diisopropyl ether.

Now, the present invention will be described in further detail with reference to Examples. However, the present invention is by no means restricted to these specific Examples. The seed crystals used in the Examples mean the compound (2).

EXAMPLE 1

Preparation of the Compound (2) Using dl-Valine in N,N-Dimethylacetamide (Without Evaporation of the Low-boiling Components)

1 g of the monohydrochloride of the compound (1), 0.58 g of dl-valine, 6 g of N,N-dimethylacetamide and 2.5 ml of 1 mol/L hydrochloric acid-dioxane solution were loaded into a 20 ml reactor and stirred at an internal temperature of 150° C. for 2 hours.

The reaction mixture was cooled to 40° C., allowed to precipitate crystals by addition of 20 g seed crystals, cooled again to an internal temperature of 10° C. and maintained at the same temperature for 1 hour.

The crystals were recovered by filtration and washed with 1 g of diisopropyl ether to afford 0.74 g of the dihydrochloride of the benzylamine compound (2).

m.p.:262° C. (decomposition).

EXAMPLE 2

Preparation of the Compound (2) Using 2-Aminoisobutyric Acid in N,N-dimethylacetamide (Without Evaporation of the Low-boiling Components)

200 mg of the monohydrochloride of the compound (1), 57 mg of 2-aminoisobutyric acid, 1.2 g of N,N- dimethylacetamide and 0.2 g of 10% (w/w) hydrochloric acid-ethanol solution were loaded into a 20 ml reactor and stirred at an internal temperature of 150° C. for 2 hours.

The reaction mixture was cooled until it precipitated crystals (to about 40° C.), then further cooled to an internal temperature of 10° C. and maintained at the same temperature for 1 hour.

The crystals were recovered by filtration and washed with 1 g of diisopropyl ether to afford 0.16 g of the desired dihydrochloride of the benzylamine compound (2) (yield 73%).

m.p.: 262° C. (decomposition).

EXAMPLE 3

Preparation of the Compound (2) Using dl-Valine in N,N-Dimethylacetamide (With Evaporation of the Low-boiling Components)

7 g of the monohydrochloride of the compound (1), 3.04 g of dl-valine, 28.89 g of N,N-dimethylacetamide and 1. of 35% concentrated hydrochloric acid were loaded into a 100 ml reactor and stirred at an internal temperature of 110–120° C. for 2 hours while the low-boiling components were evaporated.

6.45 g of N,N-dimethylacetamide was evaporated under reduced pressure, and 10.5 g of isopropyl ether was added. Then, the mixture was cooled to an internal temperature of 5° C. and maintained at the same temperature for 1 hour.

The resulting crystals were recovered by filtration and washed with a solvent mixture of 3.3 g of N,N-dimethylacetamide and 3.3 g of isopropyl ether to afford 5 g of the desired dihydrochloride of the benzylamine compound (2).

m.p.: 262° C. (decomposition).

Industrial Applicability

The present invention has established an operationally and economically advantageous process for producing the compound (2) using no protecting group.

What is claimed is:

1. A process for producing a benzylamine compound represented by formula (2), which comprises reacting a benzaldehyde compound represented by formula (1) with an amino acid in the presence of an acid.

(1)

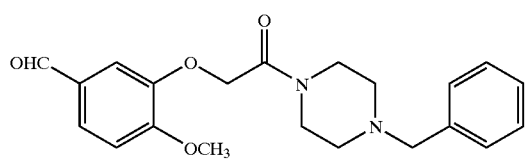

(2)

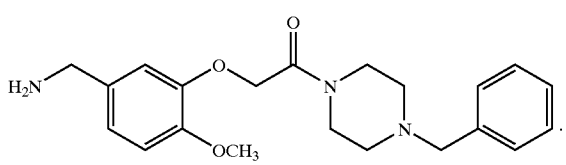

2. The process for producing a benzylamine compound according to claim 1, wherein the acid is hydrochloric acid.

3. The process for producing a benzylamine compound according to claim 2, wherein the amino acid is valine or 2-aminoisobutyric acid.

4. The process for producing a benzylamine compound according to claim 2, wherein the reaction solvent is N,N-dimethylacetamide.

5. The process for producing a benzylamine compound according to claim 2 or 4, wherein the amount of hydrochloric acid is from two to three equivalents based on the benzaldehyde compound.

* * * * *